United States Patent [19]

Eckert

[11] Patent Number: 4,528,161

[45] Date of Patent: Jul. 9, 1985

[54] PROBE FOR AUTOMATED LIQUID DISPENSER

[75] Inventor: John F. Eckert, San Rafael, Calif.

[73] Assignee: American Hospital Supply Corp., Evanston, Ill.

[21] Appl. No.: 297,960

[22] Filed: Aug. 31, 1981

[51] Int. Cl.³ .................................................. B01L 3/02
[52] U.S. Cl. ................................. 422/100; 73/864.01; 222/191; 222/527
[58] Field of Search ........... 73/864.01, 864.16, 864.18; 222/527, 530, 191; 239/525, 526, 288.5; 128/218 A, DIG. 1, DIG. 12; 422/100; 433/80, 81, 88, 91, 92, 89

[56] References Cited

U.S. PATENT DOCUMENTS

| | | | |
|---|---|---|---|
| 2,622,765 | 12/1952 | Gilmont | 422/100 |
| 3,478,430 | 11/1969 | Park et al. | 433/80 |
| 3,753,292 | 8/1973 | Hutson | 433/96 |
| 3,764,041 | 10/1973 | Noll | 422/100 |
| 4,108,608 | 8/1978 | Maher et al. | 422/100 |

FOREIGN PATENT DOCUMENTS

| | | | |
|---|---|---|---|
| 2838054 | 3/1980 | Fed. Rep. of Germany | 222/527 |
| 2920009 | 11/1980 | Fed. Rep. of Germany | 433/80 |
| 4469 | of 1884 | United Kingdom | 222/527 |
| 2062493 | 5/1981 | United Kingdom | 422/100 |

Primary Examiner—Michael S. Marcus
Attorney, Agent, or Firm—James F. Mitchell

[57] ABSTRACT

A hand-held manipulative probe for automated liquid dispensers for dispensing reagents or diluting samples with reagent automatically in accord with a programmed local microprocessor or remote computer control which grips the flexible pipette tubing, provides remote hand control and provides dispenser status indication.

10 Claims, 21 Drawing Figures

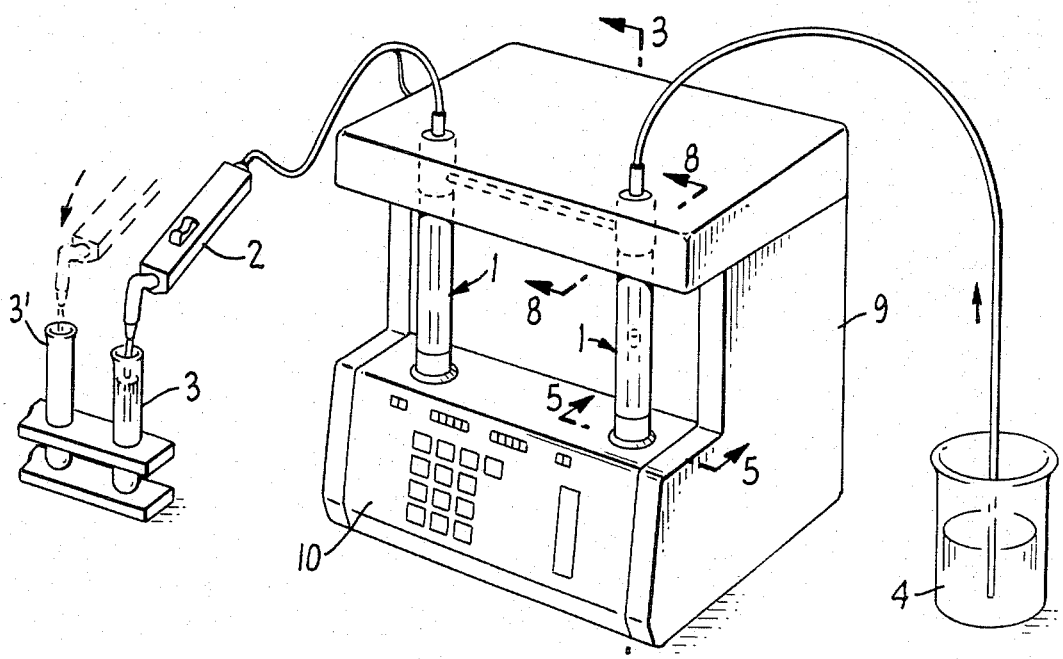
FIG. 1.
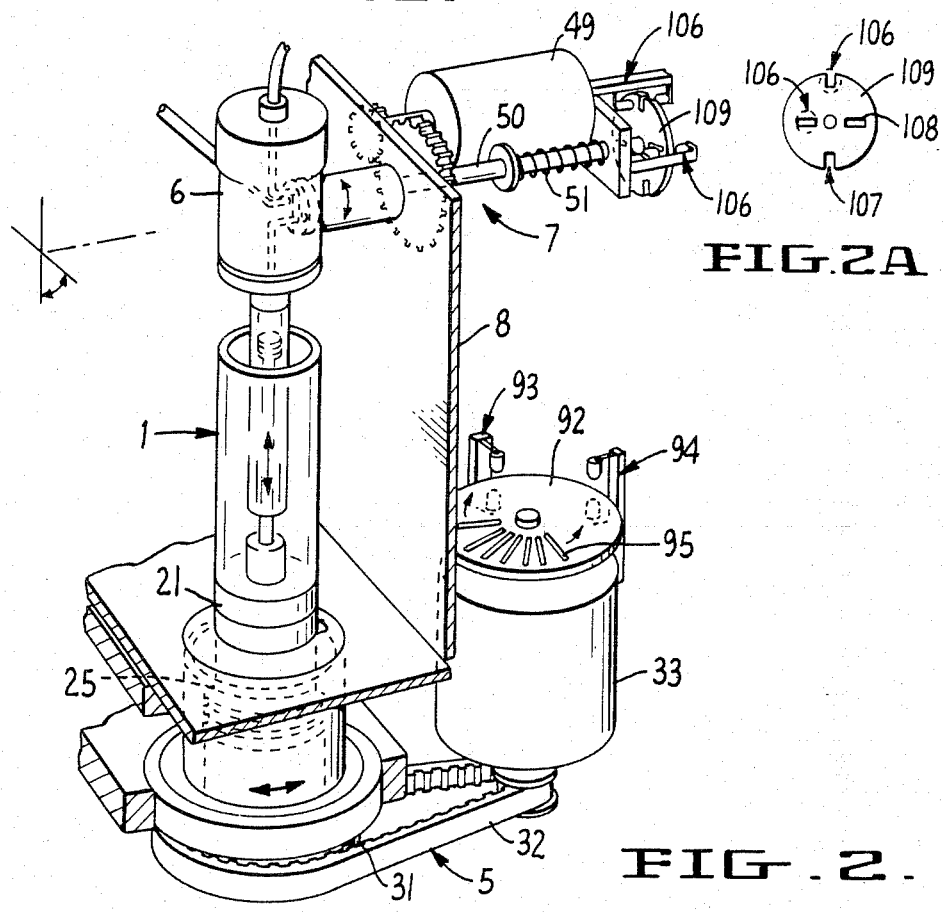
FIG. 2A.
FIG. 2.

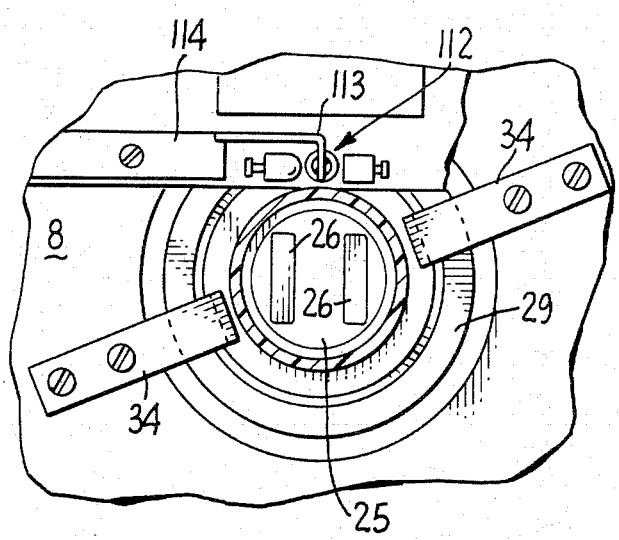
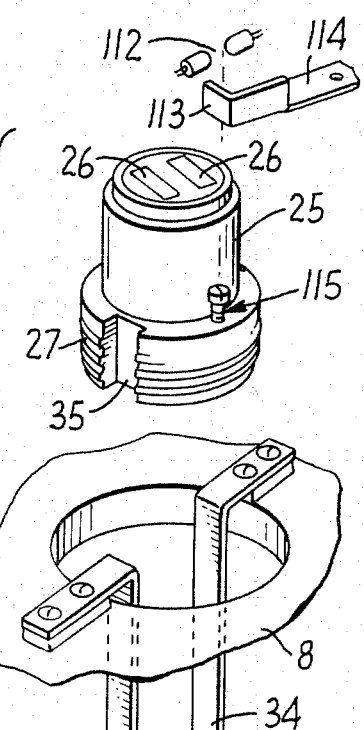
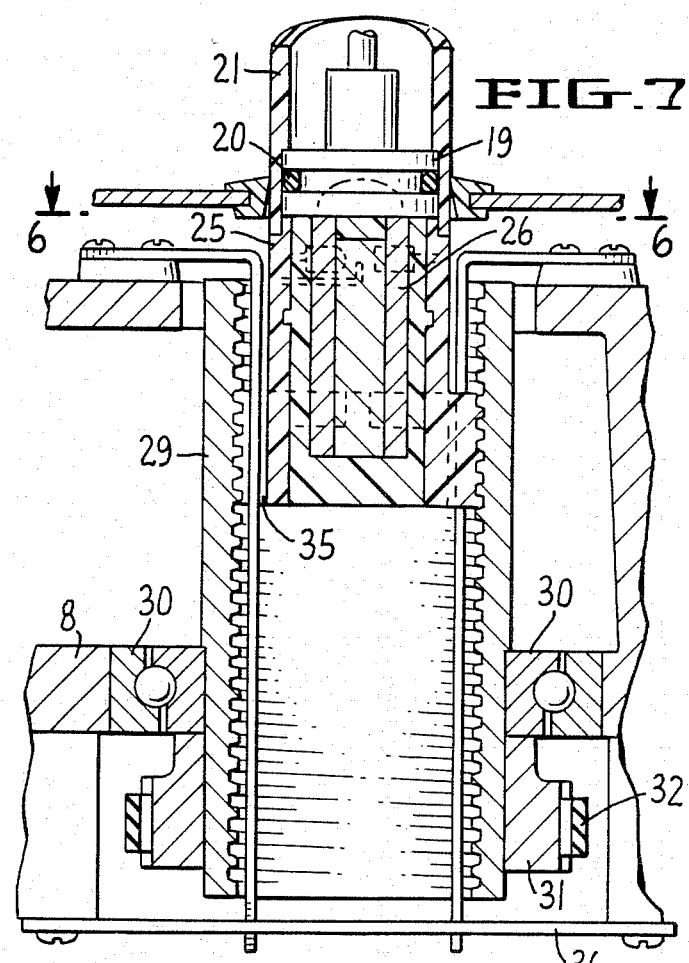
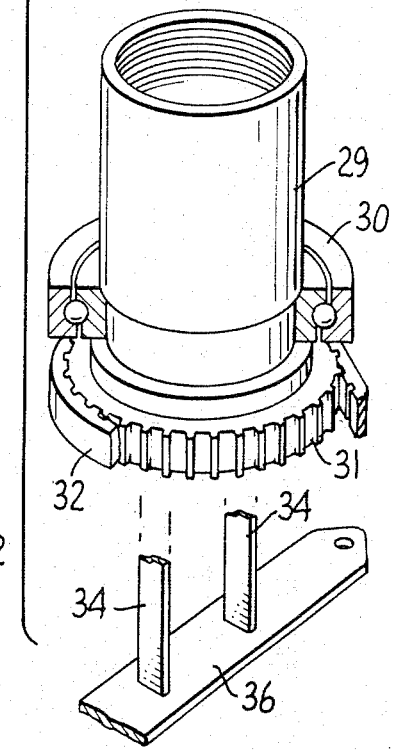
FIG. 6.
FIG. 7.
FIG. 5.

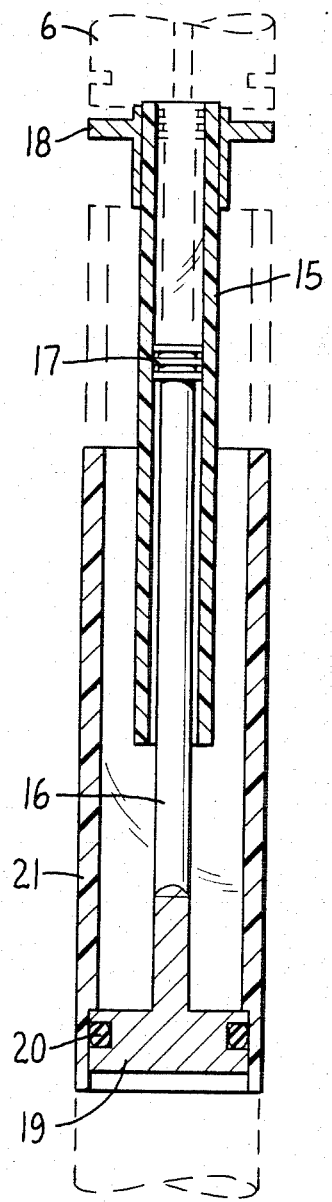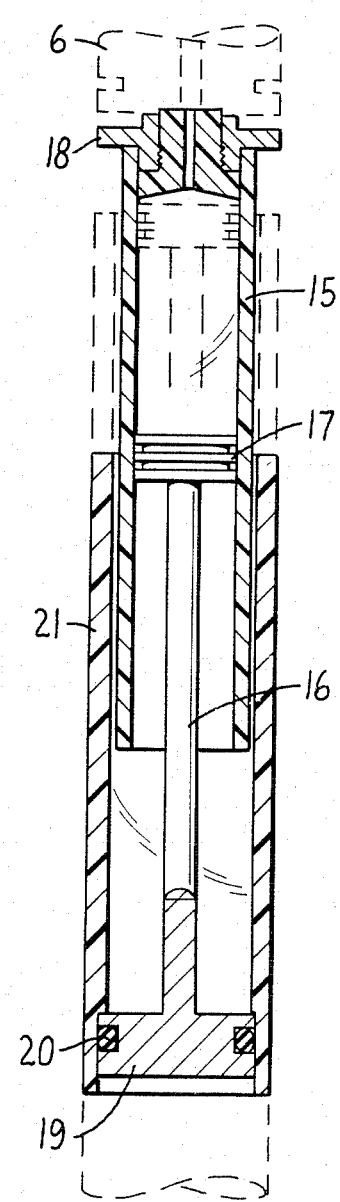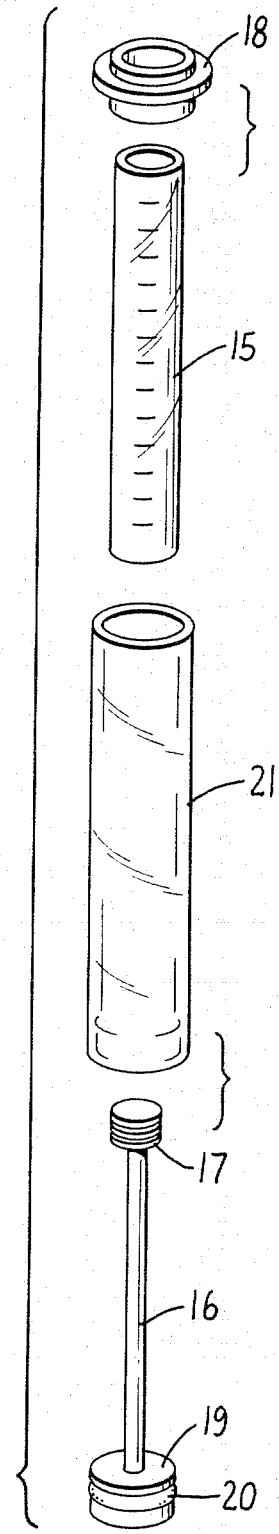
FIG. 14. FIG. 15.
FIG. 16.

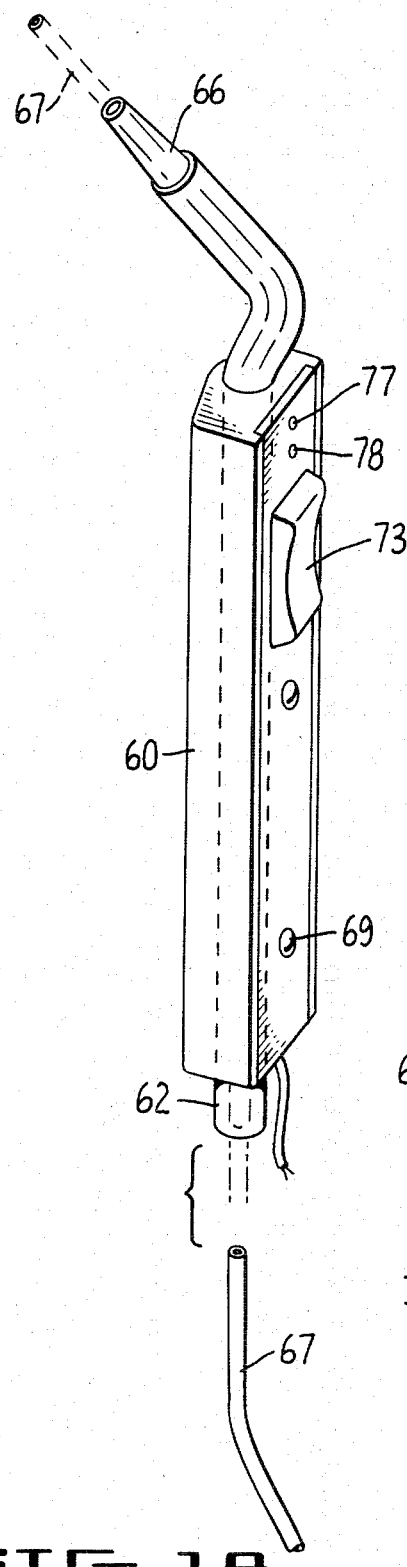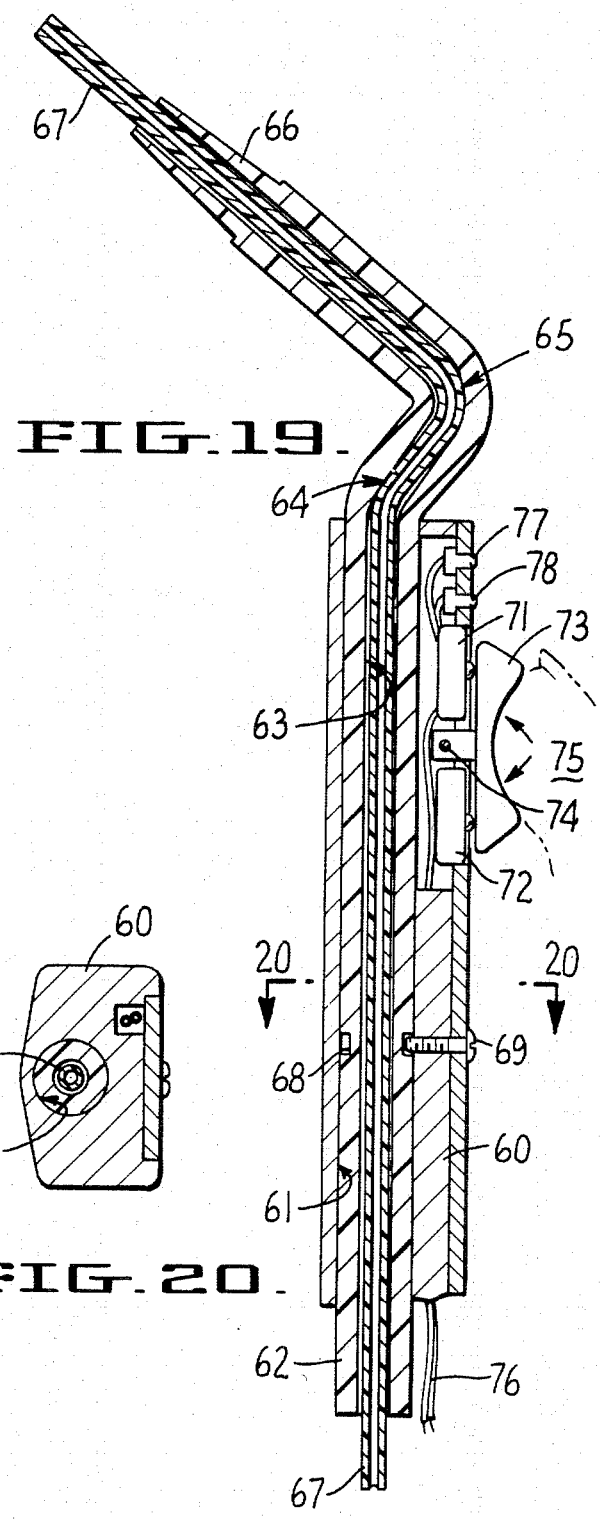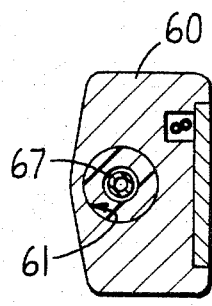
FIG.18.
FIG.19.
FIG.20.

PROBE FOR AUTOMATED LIQUID DISPENSER

This invention relates generally to automated liquid dispensers and more particularly to a manipulative probe for a bench-top laboratory instrument which employs one or more easily demountable precision metering syringes reciprocated in response to a programmed microprocessor or computer control for selectively dispensing reagent or diluting samples with reagent and other common normally manual laboratory procedures.

One object of the invention is to provide a liquid dispensing apparatus capable of local microprocessor or remote computer control.

An object of the invention also is to provide a simple hand-held manipulative probe for holding flexible pipette tubing so that it can be positioned by the operator in pipetting, sampling, purging or other mode.

Other objects and advantages of the invention will become apparent upon consideration of the following written description and the accompanying drawings wherein:

FIG. 1 is an overall perspective view of the liquid dispenser with dual syringes;

FIG. 2 is a partial perspective view illustrating a typical metering syringe and the actuator and valve means for it;

FIG. 5 is vertical sectional view of the lead-screw drive for one syringe actuator taken along line 5—5 of FIG. 1;

FIG. 6 is a top view of the lead-screw nut and its clamping arrangement taken along line 6—6 of FIG. 5;

FIG. 7 is an exploded view of the internal lead-screw drive for each syringe actuator;

FIG. 14 is a vertical sectional view of a small bore syringe used in the instrument;

FIG. 15 is a vertical sectional view of a large bore syringe used in the instrument;

FIG. 16 is an exploded view of the metering syringe components;

FIG. 18 is an enlarged perspective view of the probe illustrated in FIGS. 1 and 17;

FIG. 19 is a cross-sectional view of the probe showing its internal construction; and FIG. 20 is a cross-sectional view of the probe taken along line 20—20 of FIG. 19.

The instrument illustrated in FIG. 1 is designed for actuation of two precision metering syringes. The invention also is useful in the form of a single syringe shown in FIG. 17 or more than two syringes with appropriate valving and actuator changes which will be apparent from a consideration of the following description.

Figure 17:
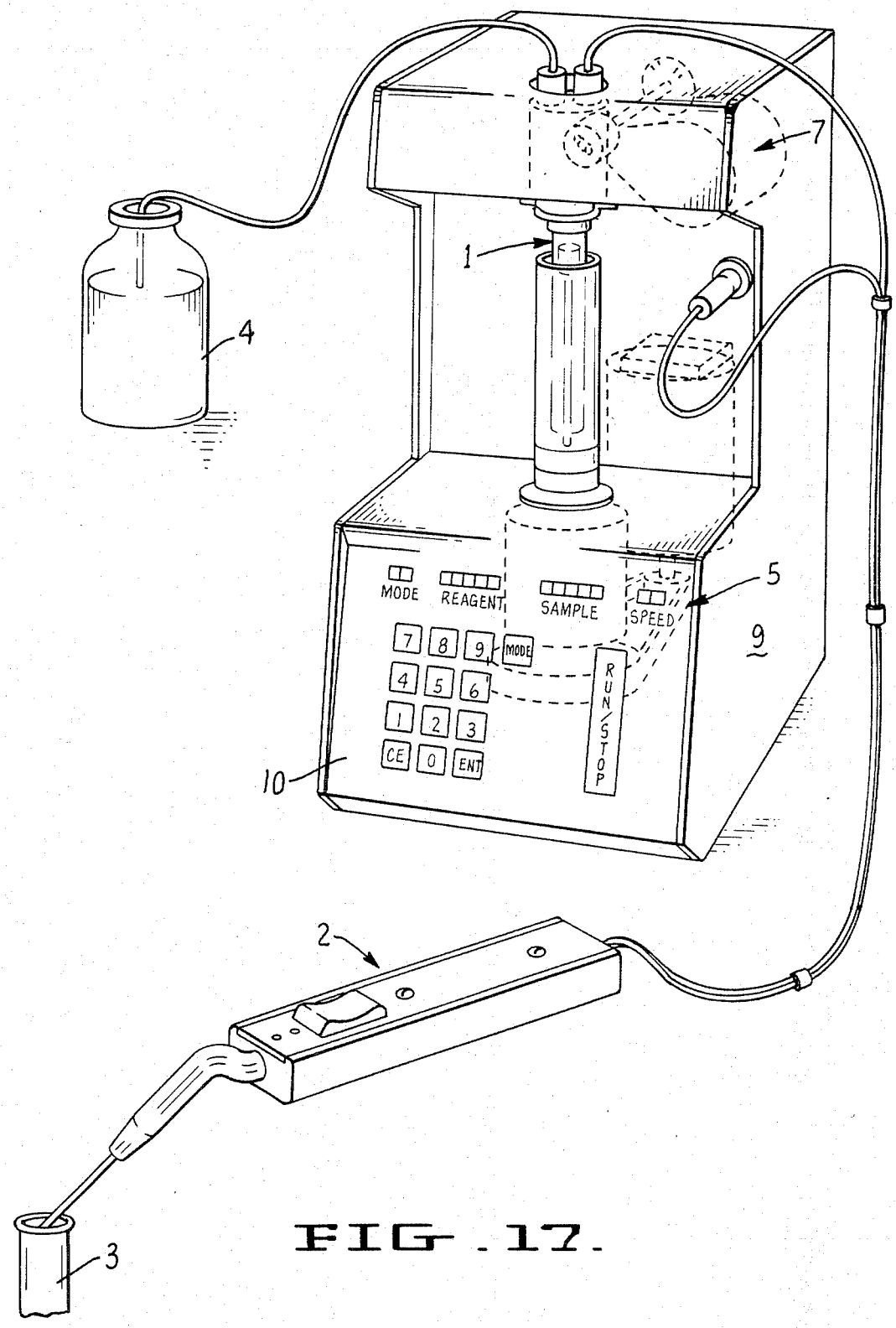
FIG. 17 is an overall perspective view of the liquid dispenser with a single syringe.

The illustrated instrument includes one or more precision metering syringes 1 arranged for drawing sample by means of probe 2 from a test tube 3, for example, or for dispensing sample or reagent-diluted sample into test tube 3', shown in hidden lines in FIGS. 1 and 17. The instrument is capable of withdrawing reagent from a reservoir, such as from beaker 4, and then using it to dilute a sample or otherwise to be dispensed from the probe 2.

Each metering syringe 1 mounts upon a syringe actuator, referred to generally as 5, in FIG. 2 at its rod end and is in fluid-tight communication with valve means 6 in FIG. 2. The syringe actuator 5, valve means 6 and its valve actuator, referred to generally as 7, mount upon a rigid frame 8. A housing 9 of chemical resistant material encloses the working components of the instrument apart from the metering syringes which are open for observation and ease of removal and replacement. A keyboard 10 for local microprocessor control mounts on the housing 9 on the front of the instrument adjacent to the metering syringes.

Each metering syringe, as is more particularly shown in FIGS. 14–16, comprises a precision ground glass cylinder 15 and a piston 16 carried on a piston rod 17 reciprocable within the cylinder. A connecting flange and seat 18 seals upon the blind end of the cylinder. The seat fits within a recess in the valve means 6 that mounts upon the frame 8. The connecting flange 18 is clamped to the valve means 6 by clamp 22 and set-screw 23.

The end of the piston rod 17 remote from piston 16 carries a mounting flange 19 made from magnetic material. In the particular embodiment illustrated, the mounting flange 19 carries on its periphery an o-ring 20 with which to secure to the flange a centering sleeve 21. The centering sleeve, as is more particularly illustrated in FIG. 7, centers the mounting flange 19 upon the end of an externally threaded lead-screw nut 25 over which the sleeve fits. The nut 25 carries permanent magnet 26 which holds the flange 19 of magnetic material firmly to the top of the lead-screw nut centered thereon by sleeve 21. The sleeve 21 sealed by o-ring 20 to mounting flange 19 also functions as an open reservoir to contain leaks or provide spill protection should a fragile glass syringe break or fracture.

The external thread 27 on the lead-screw nut 25 threads upon corresponding threads formed on the internal surface of lead-screw sleeve 29 which is rotably mounted in ball bearings 30 upon frame 8. The sleeve 29 is rotated by a toothed belt gear 31 and drive belt 32 by servo motor drive means 33 shown in FIG. 2.

The lead-screw nut 25 is restrained from rotation relative to this sleeve 29 by the pair of brackets 34 mounted at one end upon the frame 8 as shown in FIG. 7 and passing through slots 35 formed in the lead-screw nut 25. The brackets are secured at the bottom ends also to the frame 8 by means of a slotted plate 36 which fits over the free end of each bracket and is screwed to the frame as is illustrated in FIG. 5.

Figure 3:
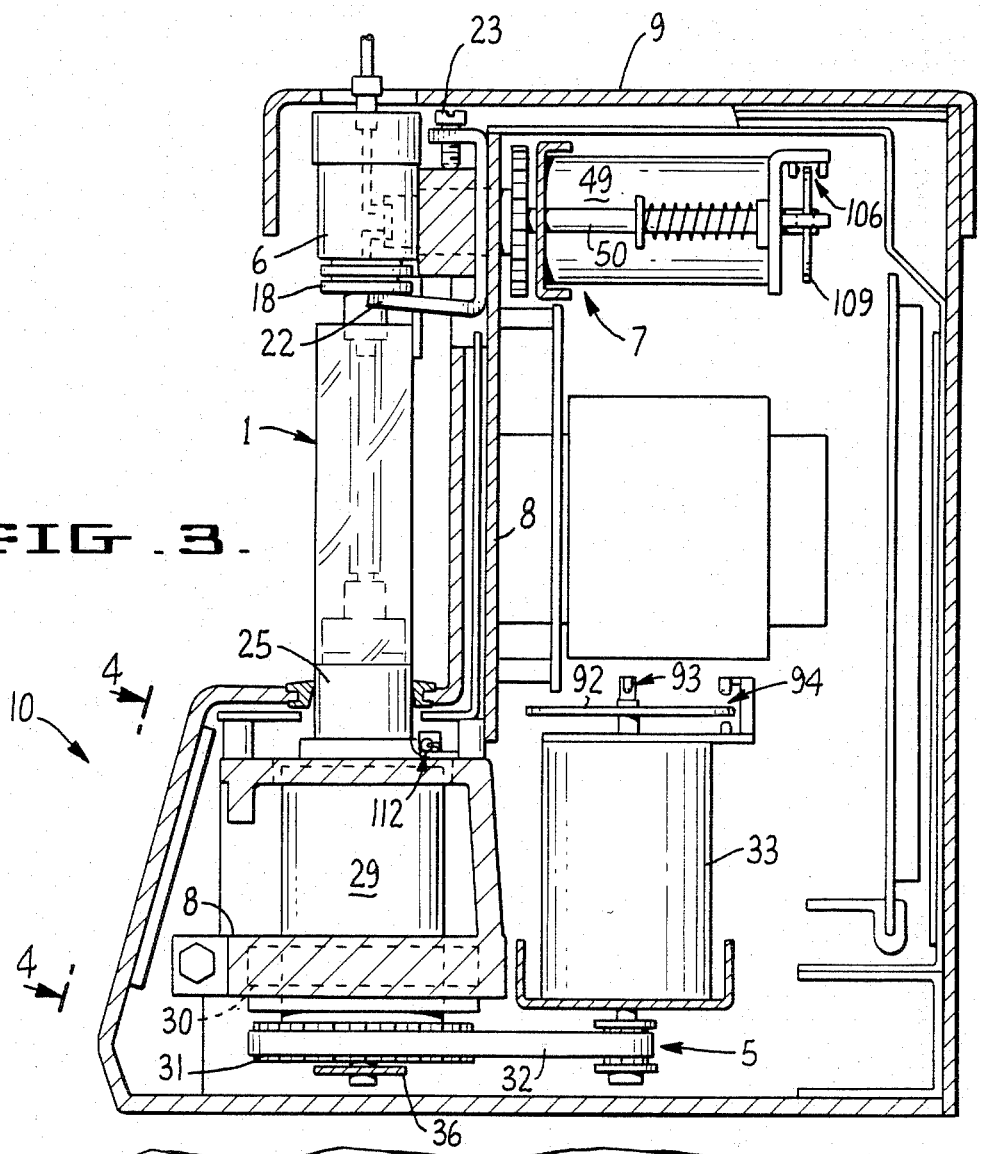
FIG. 3 is a vertical cross-sectional view of the instrument taken along line 3—3 of FIG. 1.
Figure 4:
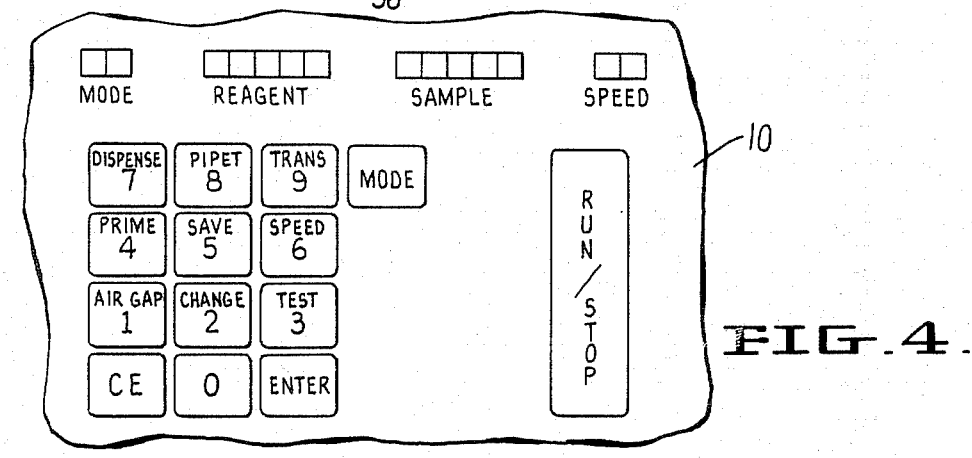
FIG. 4 is a plan view of one form of keyboard for the instrument taken along line 4—4 of FIG. 3.
Figure 9:
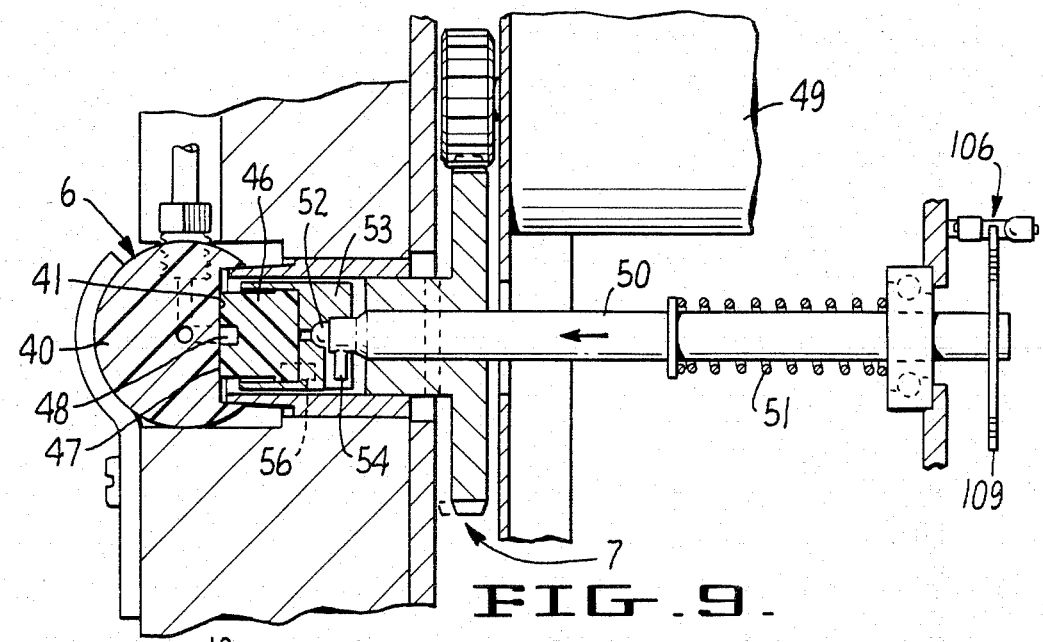
FIG. 9 is a plan view partly in section of the valve means and valve actuator taken along line 9—9 of FIG. 8.
Figure 8:
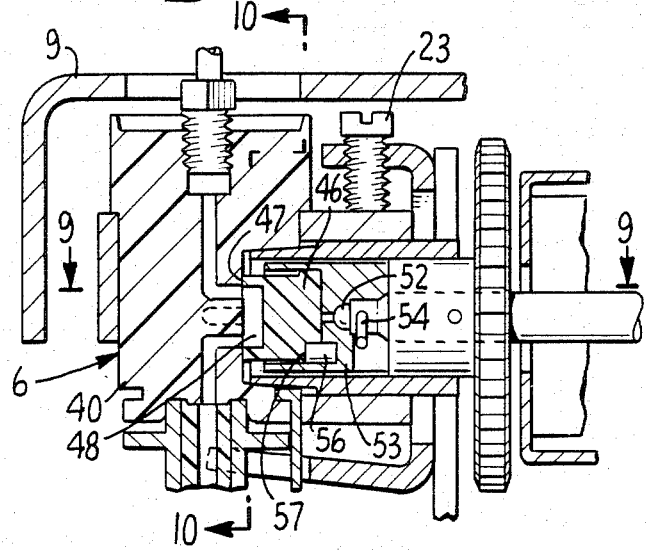
FIG. 8 is a vertical sectional view of the valve means for each syringe taken along line 8—8 of FIG. 1.
Figure 10:
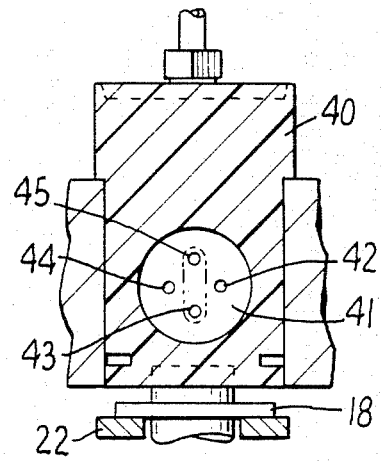
FIG. 10 is a vertical, partially sectional view of the valve means taken along line 10—10 of FIG. 8.
Figure 11:
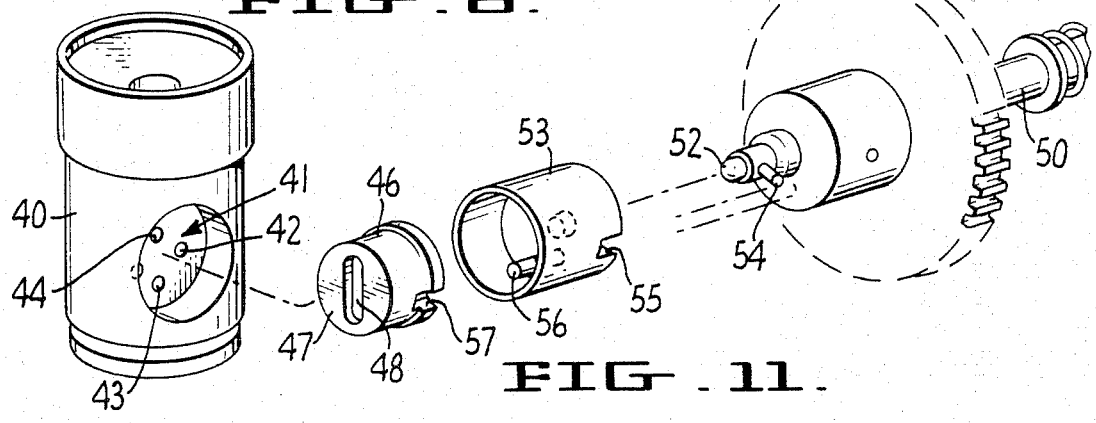
FIG. 11 is an exploded view of the valve means and valve actuator for each metering syringe.
Figure 12:
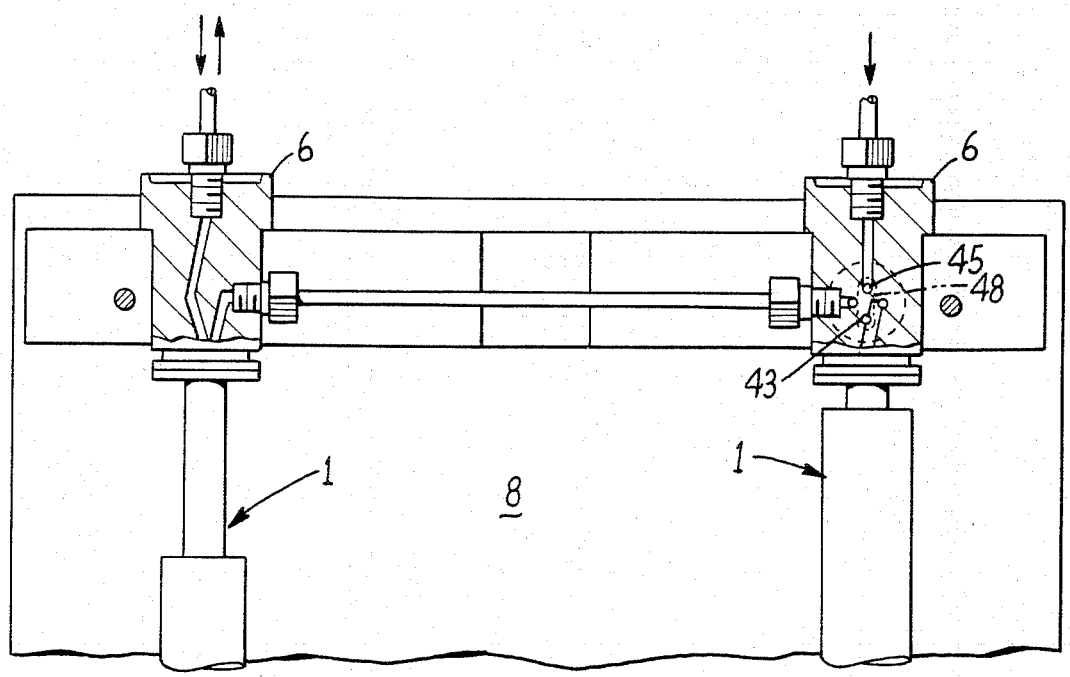
FIG. 12 illustrates the valving configuration for a dispenser with two syringes as shown in FIG. 1.
Figure 13:
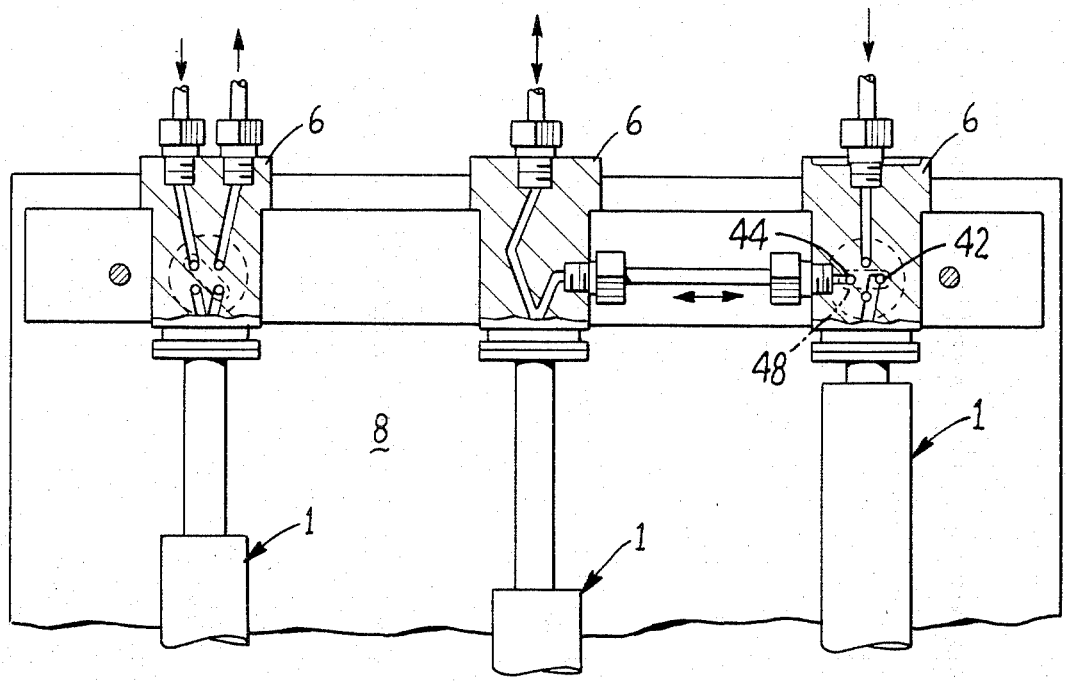
FIG. 13 illustrates the valving arrangement for a dispenser with three syringes for example.

The valve means 6 mounted in fluid communication with the blind end of each metering syringe is more particularly shown in FIGS. 8–11. Each includes a valve body 40 having a generally planar valve seat 41 bored with four ports 42, 43, 44 and 45 as illustrated in FIG. 10. The illustrated ports are in diametrically opposed pairs and each is equidistant from the rotational axis of a mating rotor 46. The spring-loaded rotor 46 has a replaceable seating face 47 having a fluid communication groove 48 on its valving face which communicates pairs of the ports 42-45 with one another in a programmed selection sequence by valve actuator means 7. The valve actuator may be a gearhead motor or include a drive motor 49 geared to a drive shaft 50 that is biased by spring 51, ball 52 and sleeve 53 against the rotor 46 to hold the rotor in fluid-tight seating relationship with the valve seat 41. The pin 54 carried on drive shaft 50 mates with a recess 55 in the sleeve 53 and pin 56 on the sleeve mates with recess 57 in rotor 46 to enable the actuator means 7 to rotate the groove 48 into selected communication among the valve ports 42-45.

Operation of the dispenser is automated by a local microprocessor control using keyboard 10 and described more particularly in co-pending application Ser. No. 297,956. The dispenser operation also can be controlled by a programmed remote computer. In either case the microprocessor controls the stroke and speed and senses the instantaneous position of each piston in the metering syringes in a manner there described so that those parameters can be varied upon command inputed through the keyboard 10 or remote computer interface.

Various modes of operation may be selected and preprogrammed into the microprocessor including the basic liquid transfers of drawing fluid into each syringe from the reagent reservoir, dispensing fluid from the syringe into the reagent reservoir, drawing fluid into the syringe from the sample probe tube or dispensing fluid from the syringe into the sample probe. Various modes of operation are obtainable including a dispense mode wherein a measured volume of liquid is drawn into a syringe from the reagent reservoir and then dispensed into the sample probe. In a pipette/dilute mode a measured volume of liquid is drawn from the reagent reservoir and then one or more separate samples are aspirated into the sample probe with air gaps separating one sample from another and from the reagent. Then the total content of the syringe may be dispensed back out through the sample probe. Various wash, purge and other modes can also be programmed into the microprocessor.

The hand held probe 2 may carry electrical switches for actuating the delivery and aspiration cycles by energizing the valve actuator 7. The probe also may include indicating means showing the instanteous position in the sequential mode of operation. The probe handle clamps to chemically inert tubing communicating it with the valve means 6 for one or several of the metering syringes. The tubing is bundled with electric conductors connecting the probe switches, microprocessor and valve actuating means.

The particular hand-held probe illustrated in FIGS. 1 and 17 is shown in more detail in FIGS. 18-20. It comprises a handle 60 formed of an elongated bar of tubular or rectangular cross-section material, such as plastic, having a longitudinal circular bore 61 in the embodiment shown. A tube holder 62 fits within the bore preferrably in an interference fit. The tube holder is generally tubular in shape with internal bore 63 and at the one end has a goose-neck configuration with a pair of reverse curves 64, 65. The tube holder 62 ends beyond the goose-neck in a nose portion 66.

The tube holder 62 carries within it Teflon flexible pipette tubing 67 frequently used in pipetting which communicates with the valve means 6. The tubing 67 trains through the internal bore 63 of holder 62. The reverse curves at 64 and 65 provide interference or frictional engagement of the tubing 67 against the interior walls of the bore 63 and hold the tubing 67 firmly within the tube holder 62 during normal operation. On the other hand, tubing 67 can easily be replaced by pulling it out of the tube holder and inserting another piece of Teflon pipette tubing. The tube holder may be secured within handle 60 by an annular groove 68 around its periphery and a set screw 69 as shown in FIG. 20. This arrangement permits the operator to twist the tube holder within handle 60 to provide any 360° orientation for the nose portion 66 as the operator sees fit. The interference fit holds the selected orientation.

In the probe 2 illustrated in FIGS. 18-20 a pair of pressure switches 71, 72 mount in handle 60 adjacent to a push button 73 pivoted at 74 by the pressure of the thumb 75 of the operator into contact with one or the other of pressure switches 71,72. Appropriate electrical conductors 76 connect the probe switches 71,72 to the microprocessor and electronic valve acuating means mounted on the dispenser frame. The probe 2 also may include indicating means such as light emitting diodes 77,78 to indicate the instaneous state of the dispener's sequential mode of operation. For example, LED 77 may light to indicate that the probe is ready to dispense sample or reagent and/or LED 78 may light to indicate the probe is ready to draw in sample or reagent.

Various modifications of the described dispenser will become apparent to those skilled in the art within the scope of the invention that is defined in the following claims.

I claim:

1. A hand-held probe for manipulating and holding flexible pipette tubing trained completely through it in an automated liquid dispenser comprising
    a handle having two ends and a linearly, axially extending interal bore therebetween;
    a tube holder partially sleeved within the handle bore and itself having a central bore for receiving a flexible pipette tubing trained completely through it,
    said tube holder comprising a linearly extending portion between the ends of said handle and a gooseneck shaped portion located external of said handle,
    said goose-neck shaped portion having first and second serially disposed reverse curve sections adjacent the handle to embrace and to restrain movement of a flexible pipette tubing only by frictional engagement of it against the walls of the central bore at the reverse curve sections.

2. The probe of claim 1 wherein the tube holder is rotatable in the handle bore with an intereference fit for orientation of the reverse curve sections as desired by the operator with respect to the handle.

3. The probe of claim 2 wherein the tube holder has an annular groove and receives a set screw mounted on the handle to secure the tube holder within the handle.

4. The probe of claim 1 further comprising
    at least one pressure switch mounted on the handle; and
    push button means for selectively actuating the pressure switch by manipulation of the operator's thumb of the hand which grips the probe.

5. The probe of claim 1 further comrising at least one indicating means for showing the state of the mode of operation of the dispenser.

6. A hand-held probe for a liquid dispenser comprising a handle having an internal bore;

a tube holer sleeved within the handle bore and itself having a central bore for receiving any portion of flexible pipette tubing trained completely through it, a length of flexible pipette tubing connected at one end to a liquid dispenser and trained completely through said tube holder central bore;

one end of the tube holder central bore having first and second serially disposed reverse curve sections embracing said tubing to restrain movement of the flexible pipette tubing only by frictional engagement of it against the walls of the central bore at the reverse curve sections.

7. The probe of claim 6 wherein the tube holder is rotatable in the handle bore with an interference fit for orientation of the reverse curve sections as desired by the operator with respect to the handle.

8. The probe of claim 7 wherein the tube holder has an annular groove and receives a set screw mounted on the handle to secure the tube holder within the handle.

9. The probe of claim 6 further comprising at least one pressure switch mounted on the handle; and push button means for selectively actuating the pressure switch by manipulation of the operator's thumb of the hand which grips the probe.

10. The probe of claim 6 further comprising at least one indicating means for showing the state of the mode of operation of the dispenser.

* * * * *